United States Patent [19]

Chao et al.

[11] Patent Number: 4,695,666

[45] Date of Patent: Sep. 22, 1987

[54] PHOSPHORUS-CONTAINING ALUMINA CATALYST FOR THE ISOMERIZATION OF AROMATICS

[75] Inventors: Tai-Hsiang Chao, Mt. Prospect; J. W. Adriaan Sachtler, Des Plaines, both of Ill.

[73] Assignee: UOP Inc., Des Plaines, Ill.

[21] Appl. No.: 944,910

[22] Filed: Dec. 22, 1986

Related U.S. Application Data

[60] Continuation-in-part of Ser. No. 871,968, Jun. 9, 1986, Pat. No. 4,654,455, which is a division of Ser. No. 806,984, Dec. 9, 1985, Pat. No. 4,636,483.

[51] Int. Cl.$^4$ ................................................. C07C 5/22
[52] U.S. Cl. ...................................... 585/481; 585/482
[58] Field of Search ................................ 585/481, 482

[56] References Cited

U.S. PATENT DOCUMENTS 4,512,876  4/1985  Miale et al. ........................ 585/481
4,599,475  7/1986  Kresge et al. ...................... 585/481

*Primary Examiner*—Curtis R. Davis
*Attorney, Agent, or Firm*—Thomas K. McBride; John F. Spears, Jr.

[57] ABSTRACT

An improved process for the isomerization of non-equilibrium $C_8$ aromatics is presented which utilizes a novel catalytic composition. This catalyst comprises phosphorus-containing alumina, a gallium component, and crystalline aluminosilicate zeolite having a silica to alumina ratio of at least 12. The isomerization process has a particular utility for the conversion of ethylbenzene without the deleterious loss of xylene.

10 Claims, 1 Drawing Figure

EB CONVERSION VS. XYLENE LOSS

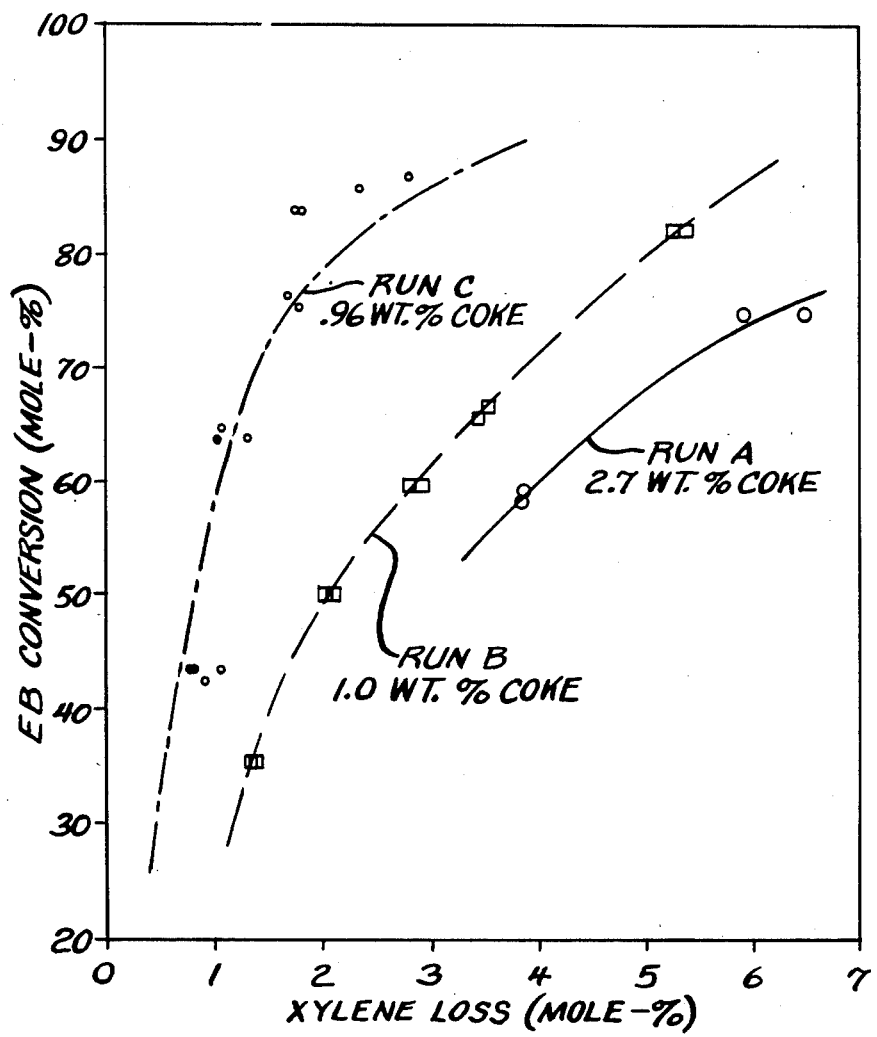

PHOSPHORUS-CONTAINING ALUMINA CATALYST FOR THE ISOMERIZATION OF AROMATICS

CROSS-REFERENCE TO RELATED APPLICATIONS

This application is a continuation-in-part of prior copending application Ser. No. 871,968 filed June 9, 1986, now U.S. Pat. No. 4,654,455, which is a division of prior copending application Ser. No. 806,984 filed Dec. 9, 1985, now U.S. Pat. No. 4,636,483. All of the teachings of said prior applications are specifically incorporated herein by reference.

BACKGROUND OF THE INVENTION

This invention relates to an improved process for the catalytic isomerization of xylenes and conversion of ethylbenzene. More specifically, it relates to a process utilizing a catalyst composition comprising a crystalline aluminosilicate zeolite, a gallium component, and phosphorus-containing alumina.

Isomerization of xylenes is industrially performed by the steps, in suitable combinations, of isomerizing an aromatic hydrocarbon feedstock containing mainly xylene isomers, separating a specified xylene isomer, normally paraxylene, from the resulting isomerization reaction mixture, and recycling the mixture left after separation. It is industrially significant in this case, for an increased efficiency of the isomerization reaction and a reduced cost of production, to adjust the composition of the xylene isomers in the isomerization reaction product as closely as possible to the thermodynamic equilibrium composition, and to inhibit side-reactions such as the decomposition of xylenes (particularly, by hydrogenation of the benzene ring, dealkylation of a methyl group, and disproportionation).

Many methods for isomerizing xylenes have been suggested in the past and many of them involve the use of a crystalline aluminosilicate zeolite-containing catalyst. Crystalline aluminosilicates generally referred to as zeolites, may be represented by the empirical formula:

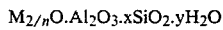

$$M_{2/n}O \cdot Al_2O_3 \cdot xSiO_2 \cdot yH_2O$$

in which n is the valence of M which is generally an element of Group I or II, in particular, sodium, potassium, magnesium, calcium, strontium, or barium, and x is generally equal to or greater than 2. Zeolites have skeletal structures which are made up of three-dimensional networks of $SiO_4$ and $AlO_4$ tetrahedra, corner linked to each other by shared oxygen atoms. The greater the proportion of the $SiO_4$ species to the $AlO_4$ species, the better suited the zeolite is for use as a component in isomerization catalysts. Representative of zeolites having such high proportion of $SiO_4$ include mordenite and the ZSM variety. In addition to the zeolite component, certain metal promoters and inorganic oxide matrices have been included in isomerization catalyst formulations. Examples of inorganic oxides include silica, alumina, and mixtures thereof. Metal promoters such as Group VIII or Group III metals of the Periodic Table, have been used to provide a dehydrogenation functionality. The acidic function can be supplied by the inorganic oxide matrix, the zeolite, or both.

A commercially viable isomerization process is one that concurrently meets the following objectives. First, the process must exhibit high xylene isomerization activity and, second, it must produce the desired product without a significant loss of xylenes. This loss is a result of undesired side-reactions, involving hydrogenation of the aromatic ring, hydrogenolysis, demethylation, and particularly disproportionation and transalkylation.

Another factor of importance in a xylene isomerization process is the effect that ethylbenzene has on the entire isomerization and xylene recovery loop. When ethylbenzene, which is normally present in 8 carbon atom aromatic fractions, is present in appreciable quantities in the feed to the isomerization process, it will accumulate in the loop unless it is excluded from the feed or converted by some reaction in the loop to products which are separable from xylenes by means tolerable in the loop. Ethylbenzene can be separated from the xylenes of boiling point near that of ethylbenzene by extremely expensive "superfractionation". A more desirable method of eliminating the ethylbenzene is through a conversion reaction taking place simultaneously with the isomerization reaction of the xylenes. It is preferable that this ethylbenzene conversion reaction be a deethylation reaction producing benzene and ethane rather than a disproportionation reaction to benzene and diethylbenzene. The deethylation reaction preserves more xylenes and produces a high quality reaction product.

It has now been found that, if a catalyst is formulated with the components, and in the manner set forth hereinafter, an improved process for the isomerization of non-equilibrium mixed xylenes containing ethylbenzene is obtained.

OBJECTS AND EMBODIMENTS

A principal object of the present invention is to provide an improved process for the isomerization of aromatic hydrocarbons and a novel catalyst composition for same. Further, the use of this process results specifically in improved conversion of ethylbenzene with the added benefit of an exceptionally high retention of $C_8$ aromatic hydrocarbons. Other objects in applying embodiments of the instant invention include providing an efficient and effective catalyst manufacturing procedure. Accordingly, a broad embodiment of the present invention is directed toward a process for isomerizing isomerizable alkylaromatic hydrocarbons which comprises contacting the alkylaromatic hydrocarbons in a reaction zone at isomerization reaction conditions with a catalytic composition comprising phosphorus-containing alumina, a gallium component, and crystalline aluminosilicate zeolite having a silica to alumina ratio of at least 12. Another embodiment is directed toward an isomerization process utilizing a catalyst comprising phosphorus-containing alumina, a gallium component, a Group VIII metal component, and crystalline aluminosilicate zeolite having a silica to alumina ratio of at least 12.

INFORMATION DISCLOSURE

The prior art recognizes numerous isomerization processes employing a variety of catalyst formulations. However, none of the prior art processes recognize the use of the catalyst formulation which is an integral part of the instant invention, nor is it apparent that these prior art processes have recognized the unique coking resistance which is characteristic of the catalyst formulation of the instant invention. Isomerization of xylenes in admixture with ethylbenzene is disclosed in U.S. Pat. No. 4,218,573, wherein a catalyst comprising ZSM-5 zeolite having a substantial alkali metal content is contacted with feed at a temperature above 427° C. This catalyst may contain a Group VIII metal, such as, nickel or platinum. The utility of a gallium component or phosphorus-containing alumina is not recognized in this reference.

U.S. Pat. 3,756,942 teaches the aromatization of $C_5$ and higher carbon number hydrocarbons utilizing a catalyst containing a ZSM-5 type crystalline aluminosilicate zeolite. This reference does not mention the utility of incorporating either a gallium component or phosphorus-containing alumina in the catalytic composite. It is also important to note that the process claim of the '942 patent is directed to a dehydrocyclization process and specifies that the catalyst is limited to use with feeds comprising from $C_5$ to an upper limit wherein at least 50 vol. % boils no higher than 121° C. This is in contrast to the present invention which is directed to isomerization of feeds comprising a non-equilibrium mixture of aromatic hydrocarbons.

The catalyst described in U.S. Pat. No. 4,157,356 does teach the utility of a gallium component for the isomerization of $C_3$–$C_8$ a hydrocarbons, but specifically limits the use of gallium to formulations containing solely silica supports. No mention is made of alternative supports or that crystalline aluminosilicate zeolites may be utilized.

U.S. Pat. No. 4,152,364 discloses a method for treating a ZSM-5 type zeolite with a phosphorus compound to deposit at least 0.5 wt. % P onto said zeolite to improve selectivity of a methylating reaction for the production of paraxylene. The '364 patent does not teach use of metals and is specific in that the phosphorus must be added directly to the zeolite.

In another reference, U.S. Pat. No. 4,270,017, which is also directed toward a process for the selective production of paraxylene, a catalyst manufacturing method is taught which involves the contacting of a calcined silica polymorph/refractory oxide composite with a phosphorus compound. This method of phosphorus addition to a calcined mixture of silica polymorph and refractory oxide does not yield the catalyst composite of the present invention. The '017 patent also does not teach the use of metals or the use of crystalline aluminosilicate zeolites.

Phosphorus is also used as an additive to improve the mechanical integrity of formed catalyst formulations. U.S. Pat. No. 3,867,279 discloses a manufacturing method to prepare a crush-resistant catalytic cracking catalyst for converting feeds having initial boiling points of at least 204° C. The '279 patent teaches the addition of a phosphorus compound to a silica sol containing a particulate silicate selected from the group consisting of silica gel, physical mixtures and cogel of silica and another refractory oxide, and crystalline aluminosilicate zeolites. This is distinguished from the catalyst composite of the instant invention in that the '279 patent specifically requires the use of a silica sol in the cracking catalyst formulation.

In brief summation, it is evident that the prior art only describes generally the use of crystalline aluminosilicate zeolites for isomerization and that no single prior art reference teaches nor suggests the combination of catalytic components used in the novel isomerization of the instant invention.

DETAILED DESCRIPTION OF THE INVENTION

This invention is concerned with the catalytic isomerization and conversion of a non-equilibrium mixture of $C_8$ aromatic hydrocarbons utilizing a novel catalytic composition comprising phosphorus-containing alumina, a gallium component, and crystalline aluminosilicate zeolite having a silica to alumina ratio of at least 12. It has been found, surprisingly and unexpectedly, that the instant process converts more ethylbenzene, preserves more aromatics, and results in less coke on catalyst than conventional isomerization processes of the prior art. This lower coking tendency increases the economic attractiveness of the isomerization process by requiring fewer catalyst regeneration cycles and increasing the on-stream efficiency, thereby increasing the production of desired aromatic product.

The process of this invention is applicable to the isomerization of isomerizable alkylaromatic hydrocarbons of the general formula $C_6H_{(6-n)}R_n$, where n is an integer from 2 to 5 and R is $CH_3$, $C_2H_5$, $C_3H_7$, or $C_4H_9$, in any combination and including all the isomers thereof. Suitable alkylaromatic hydrocarbons include, for example, orthoxylene, metaxylene, paraxylene, ethylbenzene, ethyltoluenes, the trimethylbenzenes, the diethylbenzenes, the triethylbenzenes, methylpropylbenzenes, ethylpropylbenzenes, the diisopropylbenzenes, the triisopropylbenzenes, etc., and mixtures thereof. Preferred isomerizable alkylaromatic hydrocarbons include the xylene isomers in admixture with ethylbenzene as a nonequilibrium mixture.

The isomerizable alkylaromatic hydrocarbons may be utilized as found in selective fractions from various refinery petroleum streams, e.g., as individual components or as certain boiling range fractions obtained by the selective fractionation and distillation of catalytically cracked gas oil. The process of this invention may be utilized for conversion of isomerizable aromatic hydrocarbons when they are present in minor quantities in various streams. The isomerizable aromatic hydrocarbons which may be used in the process of this invention need not be concentrated. The process of this invention allows the isomerization of alkylaromatic containing streams such as reformate to produce specified xylene isomers, particularly paraxylene, thus upgrading the reformate from its gasoline value to a high petrochemical value.

According to the process of the present invention, an alkylaromatic hydrocarbon charge stock, preferably in admixture with hydrogen, is contacted with a catalyst of the type thereinbefore described in an alkylaromatic hydrocarbon isomerization zone. Contacting may be effected using the catalyst in a fixed bed system, a moving bed system, a fluidized bed system, or in a batch type operation. In view of the danger of attrition loss of the valuable catalyst and of operational advantages, it is preferred to use a fixed bed system. In this system, a hydrogen-rich gas and the charge stock are preheated by suitable heating means to the desired reaction temperature and then passed into an isomerization zone containing a fixed bed of the catalyst previously characterized. The conversion zone may be one or more separate reactors with suitable means therebetween to ensure that the desired isomerization temperature is maintained at the entrance to each zone. It is to be noted that the reactants may be contacted with the catalyst bed in either upward, downward, or radial flow fashion, and that the reactants may be in the liquid phase, a mixed liquid-vapor phase, or a vapor phase when contacted with the catalyst.

The process of this invention for isomerizing an isomerizable alkylaromatic hydrocarbon is preferably effected by contacting the alkylaromatic, in a reaction zone containing the hereinbefore described catalyst, with a fixed catalyst bed by passing the hydrocarbon in a down-flow fashion through the bed, while maintaining the zone at proper alkylaromatic isomerization conditions such as a temperature in the range from about 0°–600° C. or more, and a pressure of atmospheric to about 100 atmospheres or more. Preferably, a temperature range of about 350°–500° C. and a pressure range of 5–15 atmospheres is desired. The hydrocarbon is passed, preferably, in admixture with hydrogen at a hydrogen to hydrocarbon mole ratio of about 0.5:1 to about 25:1 or more, and at a liquid hourly hydrocarbon space velocity of about 0.1 to about 20 $hr^{-1}$ or more, most preferably at 0.5 to 10 $hr^{-1}$. Other inert diluents such as nitrogen, argon, etc., may be present.

In accordance with the present invention, the catalytic composite comprises phosphorus-containing alumina, preferably in an amount ranging from about 20 to 99 wt. % of the composite, and most preferably ranging from 40 to 95 wt. %. What is meant by "phosphorus-containing alumina" is an inorganic, non-zeolitic, refractory oxide containing from 1:1 to about 1:100 molar ratio of phosphorus to aluminum. It is believed and further substantiated in subsequent examples, that this phosphorus-containing alumina is directly responsible for observed reduced catalyst coke levels. The phosphorus may be incorporated with the alumina in any acceptable manner known to those skilled in the art. Examples of such incorporation techniques include pilling, nodulizing, marumerization, spray drying, extrusion, or any combination of these techniques. One preferred method of preparing this phosphorus-containing alumina is in the gelation of a hydrosol precursor in accordance with the well-known oil drop method. A phosphorus compound is added to an alumina hydrosol to form a phosphorus-containing alumina hydrosol. Representative phosphorus-containing compounds which may be utilized in the present invention include: $H_3PO_4$, $H_3PO_2$, $H_3PO_3$, $(NH_4)H_2PO_4$, $(NH_4)_2HPO_4$, $K_3PO_4$, $K_2HPO_4$, $KH_2PO_4$, $Na_3PO_4$, $Na_2HPO_4$, $NaH_2PO_4$, $PX_3$, $RPX_2$, $R_2PX$, $R_3P$, $X_3PO$, $(XO)_3PO$, $(XO)_3P$, $R_3PO$, $R_3PS$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical, and X is hydrogen, R, or halide. These compounds include primary, $RPH_2$, secondary, $R_2PH$, and tertiary, $R_3P$ phosphines such as butyl phosphine, the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkylphosphates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof, such as the monopropyl ester, alkyl dialkylphosphinites, $(RO)PR_2$ and dialkyl alkylphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain 1 to 4 carbon atoms.

Other suitable phosphorus-containing compounds include: ammonium hydrogen phosphate, the phosphorus halides such as phosphorus trichloride, bromide, and iodide, alkylphosphorodichloridites, $(RO)PCl_2$, dialkylphosphorochloridites, $(RO)_2PCl$, dialkylphosphinochloridites, $R_2PCl$, alkyl alkylphosphonochloridates, $(RO)(R)P(O)Cl$, dialkylphosphinochloridates, $R_2P(O)Cl$, and $RP(O)Cl_2$. Applicable corresponding sulfur derivatives include $(RS)PCl_2$, $(RS)_2PCl$, $(RS)(R)P(S)Cl$, and $R_2P(S)Cl$.

The amount of phosphorus in the resultant catalytic composite can vary over a wide range, including from 1:0.5 to 1:100. A phosphorus to aluminum mole ratio ranging from about 1:1 to about 1:100 is preferred. The 1:1 molar ratio corresponds to a phosphorus-containing alumina containing 20.5 wt. % aluminum and 24.7 wt. % phosphorus, while the 1:100 molar ratio corresponds to 0.6 wt. % phosphorus and 52.0 wt. % aluminum.

The alumina hydrosol is typically prepared by digesting aluminum in aqueous hydrochloric acid and/or aluminum chloride solution at about reflux temperature, usually from about 80°–105° C., and reducing the chloride compound concentration of the resulting aluminum chloride solution by the device of maintaining an excess of the aluminum reactant in the reaction mixture as a neutralizing agent. The alumina hydrosol is an aluminum and chloride containing hydrosol variously referred to as an aluminum oxychloride hydrosol, aluminum hydroxychloride hydrosol, and most commonly referred to as Alsol, such as is formed when utilizing aluminum metal as a neutralizing agent in conjunction with an aqueous aluminum chloride solution. In any case, the Alsol is prepared to contain aluminum in from about a 0.70:1 to about 1.5:1 weight ratio with the chloride content thereof.

In accordance with one embodiment of the invention, a phosphorus-containing alumina is prepared by a method which comprises admixing the Alsol with a phosphorus-containing compound, the phosphorus to aluminum molar ratio in the resulting phosphorus-containing admixture being from 1:1 to 1:100 on an elemental basis and subsequently mixing in a crystalline aluminosilicate and then gelling said admixture to obtain said phosphorus-containing alumina.

In one specific embodiment, the phosphorus compound is mixed with a gelling agent before admixing with the Alsol. It is preferred that said Alsol contain a crystalline aluminosilicate zeolite. Commingling of the Alsol, containing said crystalline aluminosilicate zeolite, with the phosphorus compound-gelling agent mixture is effected by any suitable means. Resultant admixture is dispersed as droplets in a suspending medium under conditions effective to transform said droplets into hydrogel particles.

The gelling agent is typically a weak base which, when mixed with the Alsol, will cause the mixture to set to a gel within a reasonable time. In this type of operation, the Alsol is typically set by utilizing ammonia as a neutralizing or setting agent. Usually, the ammonia is furnished by an ammonia precursor which is added to the Alsol. The precursor is suitably hexamethylenetetramine, or urea, or mixtures thereof, although other weakly basic materials which are substantially stable at normal temperatures, but decompose to form ammonia with increasing temperature, may be suitably employed. It has been found that equal volumes of the Alsol and of the hexamethylenetetramine solution are satisfactory, but it is understood that this may vary somewhat. The use of a smaller amount of hexamethylenetetramine solution tends to result in soft spheres while, on the other hand, the use of larger volumes of base solution results in spheres which tend to crack easily. Only a fraction of the ammonia precursor is hydrolyzed or decomposed in the relatively short period during which initial gelation occurs.

An aging process is preferably subsequently employed. During the aging process, the residual ammonia precursor retained in the spheroidal particles continues to hydrolyze and effect further polymerization of the hydrogel whereby desirable pore characteristics are established. Aging of the hydrogel is suitably accomplished over a period of from about 1 to about 24 hours, preferably in the oil suspending medium, at a temperature of from about 60°–150° C. or more, and at a pressure to maintain the water content of the hydrogel spheres in a substantially liquid phase. The aging of the hydrogel can also be carried out in aqueous $NH_3$ solution at about 95° C. for a period up to about 6 hours. Following the aging step, the hydrogel spheres may be washed with water containing ammonia.

The phosphorus-containing alumina of the present invention may also contain minor proportions of other well-known inorganic oxides such as silica, titanium dioxide, zirconium dioxide, tin oxide, germanium oxide, chromium oxide, beryllium oxide, vanadium oxide, cesium oxide, hafnium oxide, zinc oxide, iron oxide, cobalt oxide, magnesia, boria, thoria, and the like materials which can be added to the hydrosol prior to dropping.

Another embodiment of the present invention is that the catalytic composite contain a gallium component. This component may be present in any form including elemental metal, oxide, hydroxide, halide, oxyhalide, aluminate, or in chemical combination with one or more of the other ingredients of the catalytic composite. Although it is not intended to restrict the present invention by this explanation, it is believed that the best results are obtained when the gallium component is present in the composite in the zero valency state. This gallium component can be used in any amount which is catalytically effective with good results obtained, on an elemental basis, with about 0.1 to about 5% gallium by weight of the total catalytic composite. Best results are ordinarily achieved with about 0.5 to 1 wt. % gallium, calculated on an elemental basis. Although not a necessary condition of the present invention, it is believed that a substantial portion of the gallium present in the catalyst composite is located in and/or on the crystalline aluminosilicate zeolite component.

This gallium component may be incorporated in the catalytic composite in any suitable manner known to the art to result in a relatively uniform dispersion of the gallium, such as, by ion exchange, cogelation, or impregnation either after, before, or during the compositing of the catalyst formulation. It is to be noted that it is intended to include within the scope of the present invention all conventional methods for incorporating and simultaneously uniformly distributing a metallic component in a catalytic composite and the particular method of incorporation used is not deemed to be an essential feature of the present invention. A preferred method of incorporating the gallium involves ion exchange of the crystalline aluminosilicate with a soluble compound of gallium, such as, gallium tribromide, gallium perchlorate, gallium trichloride, gallium hydroxide, gallium nitrates, gallium oxalate, and the like compounds.

As mentioned hereinabove, crystalline aluminosilicate zeolites have been successfully employed as components in catalysts used for isomerization of aromatics. In particular, a family of crystalline aluminosilicate zeolites are preferred, specifically those with silica to alumina ratios of at least 12. A particularly preferred family is the one identified as the ZSM variety. Included among this ZSM variety are ZSM-5, ZSM-8, ZSM-11, ZSM-12, ZSM-23, ZSM-35, and other similarly behaving zeolites. It is most preferred that ZSM-5 be utilized as the crystalline aluminosilicate zeolite component of the present invention. Further, it is preferred that the zeolite be substantially in the hydrogen form. These ZSM-type zeolites are generally prepared by crystallizing a mixture containing a source of alumina, a source of silica, a source of alkali metal, water, and a tetraalkylammonium compound, or its precursors. Of course, other crystalline aluminosilicates which meet the silica to alumina ratio criteria may be used, such as, faujasites, L-type, mordenites, omega-type, and the like. The relative proportions of the crystalline aluminosilicate zeolite and the other components of the catalytic composite vary widely with the zeolite content ranging from about 1% to about 80% by weight and more preferably, in the range from about 5% to 60% by weight of composite.

The catalytic composite of the instant invention may be shaped into any useful form, such as, spheres, pills, cakes, extrudates, powders, granules, tablets, etc., and utilized in any desired size. Formation usually occurs during the compositing of the catalytic components, following any known method in the art. For the purposes of the present invention, a particular useful shape of the subject catalytic composite is the sphere, manufactured by the well-known oil drop method which comprises forming an alumina hydrosol by any of the techniques taught in the art and preferably by reacting aluminum metal with hydrochloric acid and combining the resultant hydrosol with the crystalline aluminosilicate zeolite. This alumina zeolite hydrosol is commingled with a suitable gelling agent which has been contacted with a phosphorus-containing compound as previously set forth hereinabove. The resultant admixture is dispersed as droplets into an oil bath maintained at elevated temperatures. The droplets of the mixture remain in the oil bath until they set and form hydrogel spheres. The spheres are continuously withdrawn from the oil bath and typically subjected to specific aging treatments in oil and an ammoniacal solution to further improve their physical characteristics. The resulting aged and gelled particles are then washed and dried at a relatively low temperature of about 150°–205° C. and subjected to a calcination procedure at a temperature of about 450°–700° C. for a period of about 1 to about 20 hours. This treatment effects conversion of the hydrogel spheres to the desired phosphorus-containing alumina composite. See the teachings of U.S. Pat. No. 2,620,314 for additional details.

BRIEF DESCRIPTION OF THE DRAWING

Reference to the accompanying drawing may facilitate understanding of the present invention. The drawing graphically illustrates the relationship between ethylbenzene conversion, expressed as mole percent, and xylene loss, expressed as mole percent destroyed across the isomerization reaction zone.

The following example will serve to illustrate certain specific embodiments of the herein disclosed invention. This example should not, however, be construed as limiting the scope of the invention as set forth in the claims as there are many variations which may be made thereon without departing from the spirit of the invention, as those of ordinary skill in the art will recognize.

EXAMPLE

This example presents the results of three different processes. Each process was evaluated using a pilot plant flow reactor processing a feed comprising approximately 3.5 wt. % p-xylene, 68.4 wt. % m-xylene, 16.8 wt. % o-xylene, 10.3 wt. % ethylbenzene, 0.6 wt. % toluene, and the balance $C_9$ nonaromatics. The operating conditions used in the evaluation tests comprised a range of temperatures from about 370°–475° C., pressures from 5.5 to 15 atmospheres, and liquid hourly space velocities from 4 to 16 $hr^{-1}$. The temperature and space velocity were varied over the range stated in order to develop the relationship between ethylbenzene conversion and xylene retention as illustrated in the attached Figure. The pressure is increased or decreased as the temperature is varied in order to prevent an excessive formation of $C_8$ nonaromatic cyclic hydrocarbons, commonly referred to as naphthenes. It is desired to maintain a $C_8$ naphthene to $C_8$ aromatic mole ratio of less than 0.01.

Run A was conducted using a catalyst of the prior art. This catalyst comprised approximately 11 wt. % ZSM-5 zeolite, 0.29 wt. % platinum, and approximately 88 wt. % $Al_2O_3$ as the support matrix. Formulation of the catalyst by the oil drop method was as follows. Initially, the zeolite was added to an alumina sol solution, prepared by digesting metallic aluminum in hydrochloric acid, in an amount sufficient to yield a zeolite content in the finished catalyst of about 11 wt. %. A second solution of hexamethylenetetramine (HMT) was prepared and added to the zeolite/alumina sol mixture to give homogeneous admixture. This admixture was then dispersed as droplets into an oil bath maintained at about 93° C. The droplets remained in the oil bath at 150° C. until they set and formed hydrogel spheres. These spheres were removed from the oil bath, water washed with a 0.5% ammonia/water solution, air dried, and calcined at a temperature of about 650° C. These calcined spheres were then impregnated with a solution of chloroplatinic acid with 2 wt. % hydrochloric acid to yield a final platinum level of 0.29 wt. % on the finished catalyst. The impregnated spheres were oxidized and chloride adjusted at 525° C. and then subjected to a reducing environment of $H_2$ at 565° C. The isomerization performance results from Run A are presented in the accompanying FIGURE.

Run B was performed in accordance with the instant invention using a catalyst comprising approximately 50 wt. % ZSM-5 zeolite, 1 wt. % gallium, and approximately 50 wt. % phosphorus-containing alumina. The catalyst was prepared by the oil drop method in substantially the same manner as the catalyst utilized in Run A. However, in this case, phosphoric acid was added to the HMT solution, prior to commingling with the zeolite/alumina mixture, to yield a phosphorus content of the finished catalyst equal to about 12 wt. %. After the zeolite/phosphorus-containing alumina spheres were calcined, they were impregnated with a solution of gallium nitrate to achieve a level of gallium on the finished catalyst of about 1 wt. %. Also illustrated in the accompanying drawing are the test results from Run B.

Run C was similarly performed in accordance with the instant invention. The catalyst used in Run C was identical to that used in Run B except a second impregnation step using platinum tetramine dichloride was employed to add platinum to a level of about 0.18 wt. %. This impregnation solution also contained sufficient ammonium chloride to provide 2.0 wt. % chloride based on the weight of the catalyst. After the platinum impregnation, the catalyst was oxidized and chloride adjusted at 525° C. and then reduced in $H_2$ at 565° C. Again, the isomerization test results from Run C are graphically presented in the FIGURE.

In analyzing the performance of the three processes, it is desirable to focus on a particular level of ethylbenzene conversion and then examine to what extent each process preserved valuable xylene product, i.e., had the lowest xylene loss. Picking 60 mol.% ethylbenzene conversion as a basis, it is readily apparent from the Figure that the two processes of the instant invention, Runs B and C, show increased preservation of xylene product compared to the prior art process of Run A. In other words, when the prior art process is compared to the instant invention, it is evident that about 38% more xylene is destroyed than Run B and 300% more than Run C. Another important feature shown in the Figure is the reduced level of coke on spent catalyst for Runs B and C. This reduced coke compared to the prior art process allows for longer catalyst life leading to greater overall run length and thus increased production of desired xylene product.

What is claimed is:

1. A process for isomerizing isomerizable alkylaromatic hydrocarbons which comprises contacting the alkylaromatic hydrocarbons in a reaction zone at isomerization reaction conditions with a catalytic composition comprising phosohorus-containing alumina, a gallium component, and crystalline aluminosilicate zeolite having a silica to alumina ratio of at least 12.

2. The process of claim 1 further characterized in that the alkylaromatic hydrocarbons comprise a non-equilibrium mixture of xylenes containing ethylbenzene.

3. The process of claim 1 further characterized in that the isomerization reaction conditions comprise a temperature in the range from about 350° C. to about 500° C., a pressure from about 5 to about 15 atmospheres, a liquid hourly space velocity of from about 0.5 to 10 liquid volumes of the alkylaromatic hydrocarbons per hour per volume of the catalytic composition.

4. The process of claim 1 further characterized in that the crystalline aluminosilicate zeolite is selected from the group consisting of ZSM-5, ZSM-8, ZSM-11, ZSM-12, ZSM-23, and ZSM-35.

5. The process of claim 1 further characterized in that the crystalline aluminosilicate zeolite is hydrogen form ZSM-5.

6. The process of claim 1 further characterized in that the catalytic composition comprises between 40 and 95 wt. % phosphorus-containing alumina.

7. The process of claim 6 further characterized in that the phosphorus to aluminum ratio of the phosphorus containing alumina is from 1:1 to 1:100.

8. The process of claim 1 further characterized in that the catalytic composition comprises a Group VIII metal component.

9. The process of claim 8 further characterized in that the Group VIII metal component is platinum.

10. A process for isomerizing a non-equilibrium mixture of xylenes containing ethylbenzene which comprises contacting said non-equilibrium mixture with a catalytic composite comprising phosphorus-containing alumina, a gallium component, a Group VIII metal component, and a crystalline aluminosilicate zeolite selected from the group consisting of ZSM-5, ZSM-8, ZSM-11, ZSM-12, ZSM-23, and ZSM-35, at a temperature of from about 350° C. to about 450° C., a pressure from about 5 to about 15 atmospheres, and a liquid hourly space velocity of from about 0.5 to about 10 $hr^{-1}$.

* * * * *